(12) United States Patent
Sharma

(10) Patent No.: US 6,992,303 B2
(45) Date of Patent: Jan. 31, 2006

(54) DETECTING EMITTERS OF ELECTROMAGNETIC RADIATION, IN PARTICULAR FLUOROPHORE LABELED SUBSTANCES

(75) Inventor: Shiv Sharma, Amersham (GB)

(73) Assignee: Amersham Biosciences UK Limited, Amersham (GB)

( * ) Notice: Subject to any disclaimer, the term of this patent is extended or adjusted under 35 U.S.C. 154(b) by 0 days.

(21) Appl. No.: 10/496,764

(22) PCT Filed: Nov. 28, 2002

(86) PCT No.: PCT/GB02/05372

§ 371 (c)(1),
(2), (4) Date: Nov. 2, 2004

(87) PCT Pub. No.: WO03/048749

PCT Pub. Date: Jun. 12, 2003

(65) Prior Publication Data

US 2005/0051745 A1    Mar. 10, 2005

(30) Foreign Application Priority Data

Nov. 29, 2001  (GB) .................................... 0128587

(51) Int. Cl.
*F21V 9/16*      (2006.01)
*G01J 1/58*      (2006.01)

(52) U.S. Cl. ................... 250/458.1; 356/318

(58) Field of Classification Search ............... 250/205, 250/207, 208.1, 214 A, 214 AG, 559.06, 250/559.29, 458.1, 461.1, 580, 586; 356/317, 356/318
See application file for complete search history.

(56) References Cited

U.S. PATENT DOCUMENTS

| | | | |
|---|---|---|---|
| 3,902,813 A | | 9/1975 | Vanden Broek et al. |
| 4,828,400 A | | 5/1989 | Boyce |
| 5,062,942 A | * | 11/1991 | Kambara et al. ........... 204/612 |
| 5,280,367 A | | 1/1994 | Zuniga |
| 5,672,881 A | | 9/1997 | Striepeke et al. |
| 5,764,791 A | * | 6/1998 | Hara ......................... 382/132 |
| 6,043,506 A | | 3/2000 | Heffelfinger et al. |
| 6,740,898 B2 | * | 5/2004 | Yasuda ....................... 250/587 |

FOREIGN PATENT DOCUMENTS

| | | |
|---|---|---|
| WO | WO 96/23213 | 8/1996 |
| WO | WO 98/11427 | 3/1998 |
| WO | WO 02/35441 | 5/2002 |

* cited by examiner

*Primary Examiner*—Seung C. Sohn
(74) *Attorney, Agent, or Firm*—Royal N. Ronning, Jr.; Yonggang Ji

(57) ABSTRACT

The performance of devices for the detection of fluorophore labelled substances in an electrophoretic separation medium is improved by rescanning lines or pixels which caused saturation of an electromagnetic radiation detecting means (19) at a lower gain, the lower gain being adapted to prevent saturation of the electromagnetic radiation detecting means (19).

8 Claims, 3 Drawing Sheets

DETECTING EMITTERS OF ELECTROMAGNETIC RADIATION, IN PARTICULAR FLUOROPHORE LABELED SUBSTANCES

This application is a filing under 35 U.S.C. § 371 and claims priority to international patent application number PCT/GB02/05372 filed Nov. 28, 2002, published on Jun. 12, 2003 as WO 03/048749 and also claims priority to patent application number 0128587.3 filed in Great Britain on Nov. 29, 2001; the disclosures of which are incorporated herein by reference in their entireties.

TECHNICAL FIELD

The invention relates to a method and an apparatus for detecting emitters of electromagnetic radiation, in particular fluorophore labelled substances in an electrophoretic separation medium.

BACKGROUND OF THE INVENTION

When detecting fluorophore labelled substances in an electrophoretic separation medium, e.g. in connection with DNA sequencing, it is known that upon excitation, at some stage, the signal generated by a detector in response to the detected intensity of the fluorescence emitted by the substances, may fade out, e.g. due to the fact that there is too little fluorophore labelled DNA in the sample. There may also be other reasons for the signal to fade out or be too low to be detected normally.

It is also known that in some applications, e.g. fragment analysis, the opposite situation may arise, namely that the intensity of the fluorescence will be too high for the detector to handle, i.e. the detector will become saturated.

In both these cases, information about the separated substances may be lost. This can e.g. lead to that it will be impossible to determine the DNA sequence.

Proteins and carbohydrates are two other examples of substances that may be labelled with fluorophores and separated in an electrophoretic separation medium.

Patent abstracts of Japan, abstract of JP-A-7-151687, describes the prevention of reading errors of a basic sequence in a fluorescence detection type electrophoretic apparatus by monitoring the intensity of the excitation light. An alarm is generated when the detection signal from a photodetector is smaller than a predetermined reference value because of an abnormal intensity of the emission light. In another prior art device a first image of the fluorescence emitted by said fluorophore labelled substances upon illumination is acquired using a photo-multiplier tube during a first scan at a first voltage setting (and hence gain) and then a second image of the same substances is acquired by a second scan at a different PMT voltage and gain. For example, a first scan could be performed at a high gain setting of 1000 Volts in order to capture an image showing samples emitting a small amount of fluorescence. As samples emitting a high amount of fluorescence will saturate the signal at this gain and it is not possible to quantify the signals if they are saturated then a second scan at a lower voltage, e.g. 400V, which gives a lower gain, and hence gives an unsaturated signal, is necessary. This increases the dynamic range of the sensor but doubles the scanning time.

BRIEF DESCRIPTION OF THE INVENTION

The object of the invention is to eliminate the problems mentioned above.

This is attained by a first embodiment of a method according to the present invention by first scanning the image at a high gain, detecting any saturated pixels and then rescanning at a lower gain only lines or pixels on which pixel saturation has occurred.

The above object is also attained by a second embodiment of a method in accordance with present invention by first scanning the image at a high gain, detecting any pixels which exceed a predetermined intensity value, computing the peak of saturation, for example by finding the centre of the saturation edges or by fitting a Gaussian curve to the truncated edges, and then rescanning at a computed lower gain only lines or pixels on which a pixel which has exceeded the predetermined intensity value has occurred.

The above object is also attained by a first embodiment of an apparatus in accordance with the invention wherein the apparatus comprising means for scanning lines at a high gain, means for determining if a pixel in a scanned line is saturated and means for rescanning at a lower gain lines in which saturated pixels occur. The above object is also attained by a second embodiment of an apparatus in accordance with the invention wherein the apparatus comprising means for scanning lines at a high gain, means for setting a predetermined pixel intensity value means for determining if a pixel intensity in a scanned line is above said predetermined intensity value and means for computing the peak value and rescanning at a computed lower gain lines or pixels in which a pixel intensity above said predetermined intensity value occur.

Other embodiments of the present invention, described below, also achieve the above object.

BRIEF DESCRIPTION OF THE DRAWING

The invention will be described more in detail below with reference to the figures in which.

DESCRIPTION OF PREFERRED EMBODIMENTS

An embodiment of an apparatus according to the present invention for detecting emitters of electromagnetic radiation, in particular fluorophore labelled substances in an electrophoretic separation medium, is schematically illustrated.

The embodiment shown relates to scanning a gel electrophoresis apparatus in which substances migrate in the separation medium, i.e. an electrophoresis gel.

However, it is to be understood that the invention is equally applicable to scanning capillary electrophoresis and any other systems in which radiation, particularly electromagnetic radiation, is to be detected.

Moreover, the invention may be applied not only to the above direct detection methods but also to indirect detection methods, i.e. methods where, the fluorophore labelled substances are first separated in e.g. a gel, and where the gel is subsequently placed in e.g. a laser scanner to detect e.g. the order of the substances.

Figure 1:
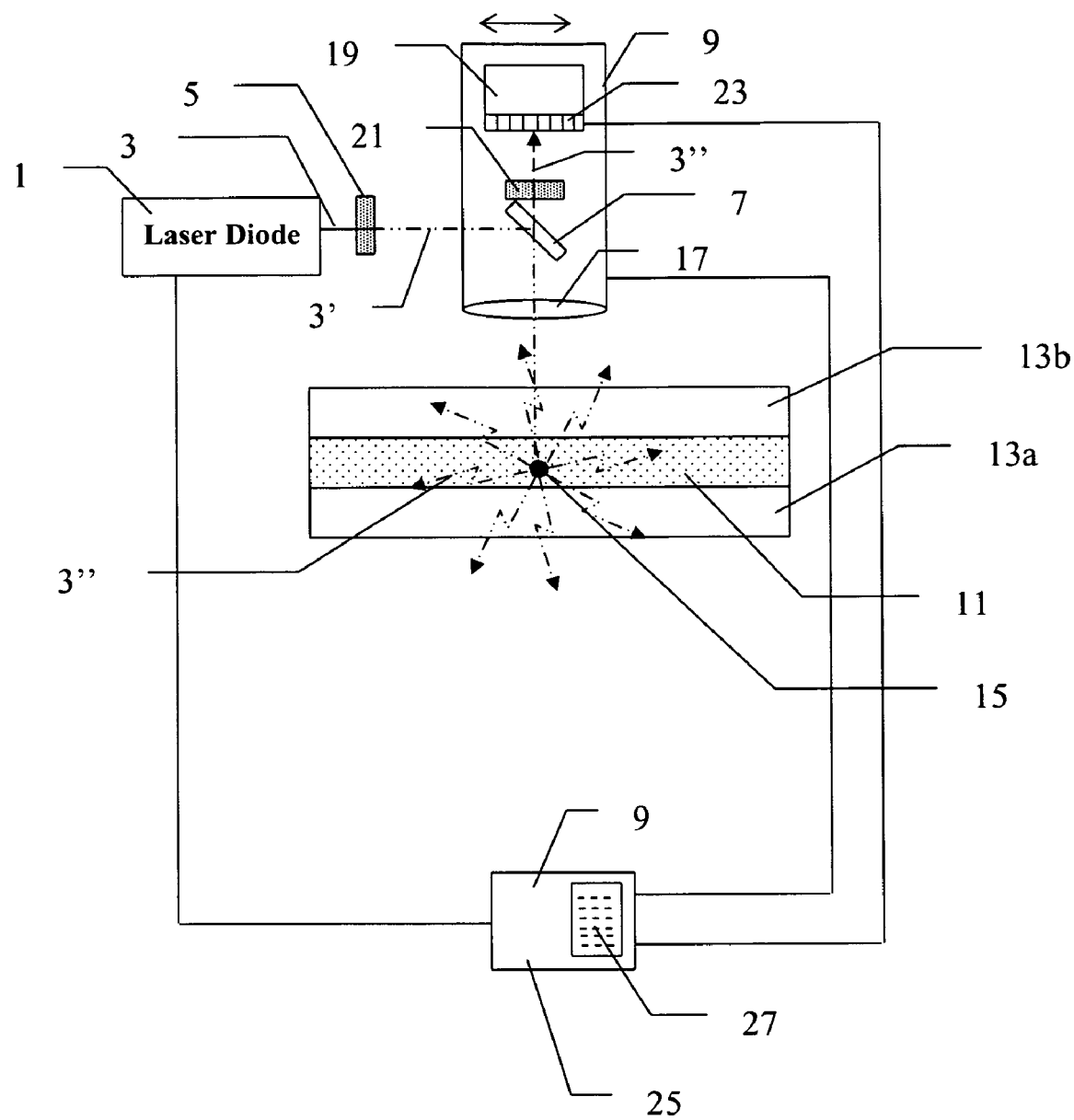
FIG. 1 shows schematically a first embodiment of an apparatus according to the present invention.

In FIG. 1, reference numeral 1 denotes a stationary illumination source. In the embodiment shown, the illumination source is a laser diode which emits a laser beam 3. However, it is conceivable that a halogen lamp or any other suitable electromagnetic radiation source may be used as illumination source.

The laser beam 3 is passed though a filter 5 which allows electromagnetic radiation of fluorophore excitation frequency Ex to pass and is aimed at a dichroic mirror 7 in a movable scanning head 9. Mirror 7 reflects the filtered laser beam 3' towards an area which is to be scanned, in this case an electrophoresis gel 11. In a manner well known per se, gel 11 is positioned between two glass plates 13a, 13b.

The gel 11 is part of an electrophoretic separation system, not shown in any greater detail, for separating substances which are labelled with a substance which emits, or is capable of emitting, electromagnetic radiation, e.g. a fluorophore 15, and which under influence of an electric field migrate along migration lanes (not shown) in the gel 11.

When a fluorophore 15 is illuminated by the laser beam 3', the fluorophore 15 is excited to emit fluorescence electromagnetic radiation 3" of frequency Em. Some of this fluorescence electromagnetic radiation 3" enters the lens 17 of the scanning head 9 (which contains an electromagnetic radiation detecting means such as a photodetector, e.g. photomultiplier tube (PMT) 19), passes through dichroic mirror 7 and a filter 21 which allows electromagnetic radiation of emission frequency Em to pass and is detected by one or more detector cells 23 in the PMT 19. The PMT 19 is adapted to generate a signal in response to the intensity of the detected emitted fluorescence electromagnetic radiation 3".

In this embodiment of the present invention, scanning head 9 is movable across the gel 11 and scans the gel 11 as it moves relative to it. It is also conceivable to have a fixed scanning head and to move the gel relative to it. It is also conceivable to have a fixed scanning head and a fixed gel and to accomplish relative movement between them by means of movable lenses and/or mirrors. The movement of the scanning head 9 or gel is controlled by a control means 25, preferably a programmable control means such as a computer 25.

On the drawing, the excitation of a single fluorophore 13 in a single migration lane is schematically indicated, but it is to be understood that in a practical embodiment of the apparatus according to the invention, there may be several, mutually parallel migration lanes in the gel 11 as well as a corresponding number of photodetectors 19.

The signals generated by the detector 23 in photodetector 19 in response to the intensity of the detected fluorescence, are analysed by software, preferably executed in control means 25, in order to determine the intensity of the emitted fluorescence electromagnetic radiation 3".

In a first embodiment of the invention, the control means 25 is adapted to set the gain of the photodetector 19 to a high level, e.g. with a voltage of 1000 V. The gel is then scanned line by line and the intensity of the signals received from the PMT 19 are monitored by control means 25. In the event of a detector cell 23' in a scan line producing a saturation signal which indicates that the intensity of emitted fluorescence electromagnetic radiation 15 reaching the PMT 19 has saturated the PMT cell 23' detecting the electromagnetic radiation, the position of the line being is stored in a memory 27. After the scan with the high PMT gain has been complete, the control means 25 sets the gain of the PMT 19 to a lower level, e.g. 400V. It then controls the rescanning of the gel 11 such that only lines or pixels in which a detector cell 23 produced a saturation signal are rescanned. The signals from this scan may be used by the control means in combination with the signals from the first scan to produce a composite image or record in which the relative intensities of fluorophores in the gel can be seen. Preferably the control means takes into account the decrease in gain used during the second scan and compensates for it when plotting the lines or pixels rescanned in the second scan.

If the number of lines which have to be rescanned is 5% of the total number of lines then a time saving of up to 95% of the time needed to scan a gel once can be achieved. In other words if in the prior art it took 200 seconds to scan a gel (100 seconds for a high gain scan and 100 seconds for a low gain scan), then with the present invention it will take 100 seconds for the high gain scan and 5 seconds (plus the time to move the scanning arrangement from line to line) for the low gain scan—a saving of up to 95 seconds.

In a second embodiment of the invention, the control means is provided with a memory in which a predetermined maximum signal intensity level can be set. This predetermined level could be set at any suitable proportion of the signal intensity needed to saturate the PMT, for example, 99%, 90%, 80%, 75% etc, when using a high gain. The scanning of the sample gel proceeds in a fashion similar to that described with respect to the first embodiment, with the difference that in the event of a cell 23 in a line producing a signal which indicates that the intensity of emitted fluorescence electromagnetic radiation 3" reaching the PMT 19 detected by a PMT cell 23' detecting the electromagnetic radiation has exceeded the predetermined maximum signal intensity then the position of the line is stored in a memory 27. After the sample has been completely scanned with the high PMT gain, the control means 25 computes the anticipated line or pixel intensity (for example by finding the centre of the saturation edges or by fitting a Gaussian curve to the truncated edges) and sets the gain of the PMT 19 accordingly to a lower level, e.g. 600V in order to prevent the PMT 19 being saturated when rescanning the line or pixel. It then controls the rescanning of the gel 11 such that only lines or pixels in which a detector cell 23 produced a signal intensity greater than the predetermined maximum signal are rescanned.

It is also possible to scan different lines or pixels of a gel sample where a pre-set threshold has been exceeded at varying pmt voltages to produce the most effective dynamic range image.

Figure 2:
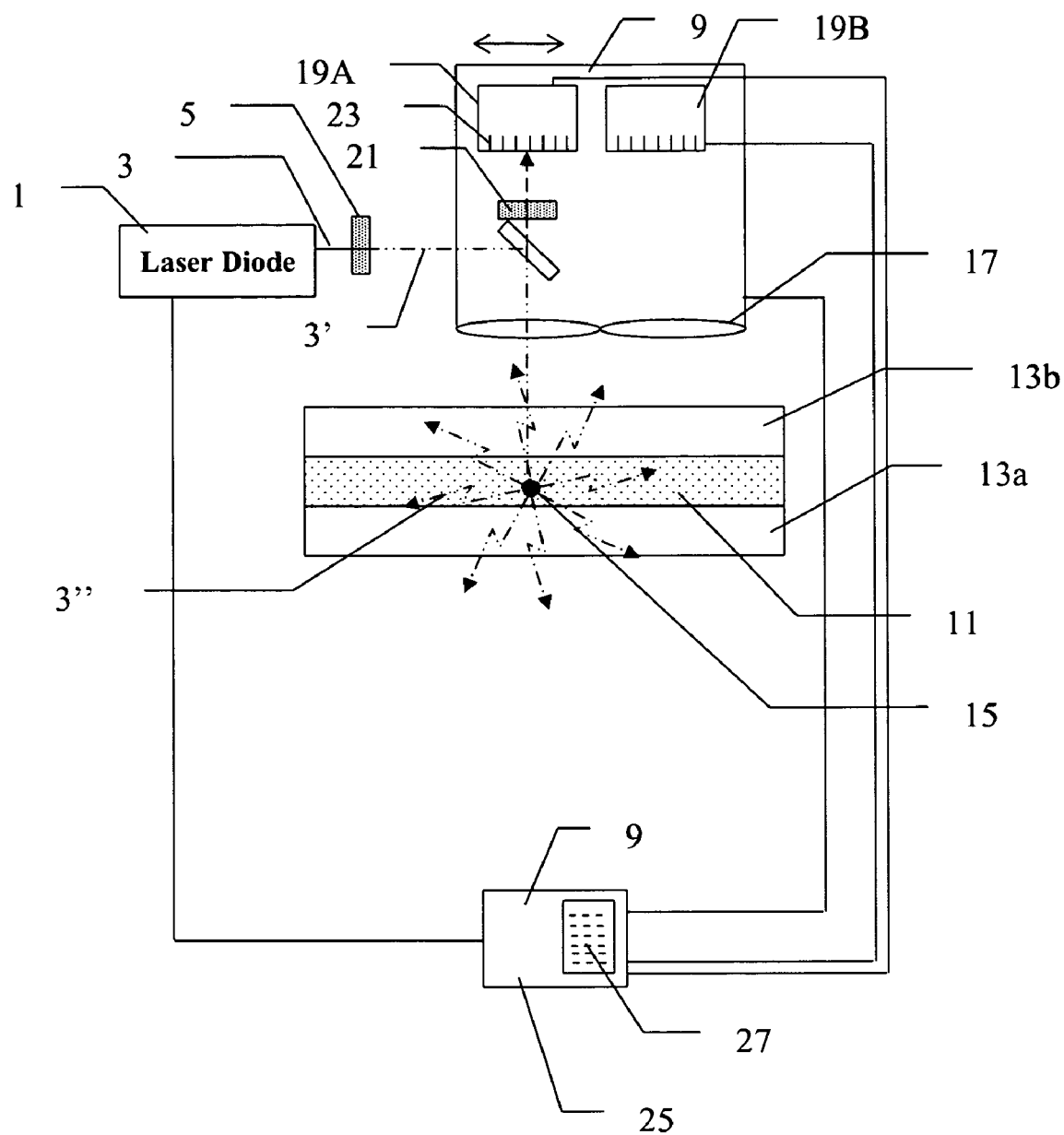
FIG. 2 shows schematically another embodiment of an apparatus according to the present invention; and, FIG. 3 shows schematically a further embodiment of an apparatus in accordance with the present invention.
Figure 3:
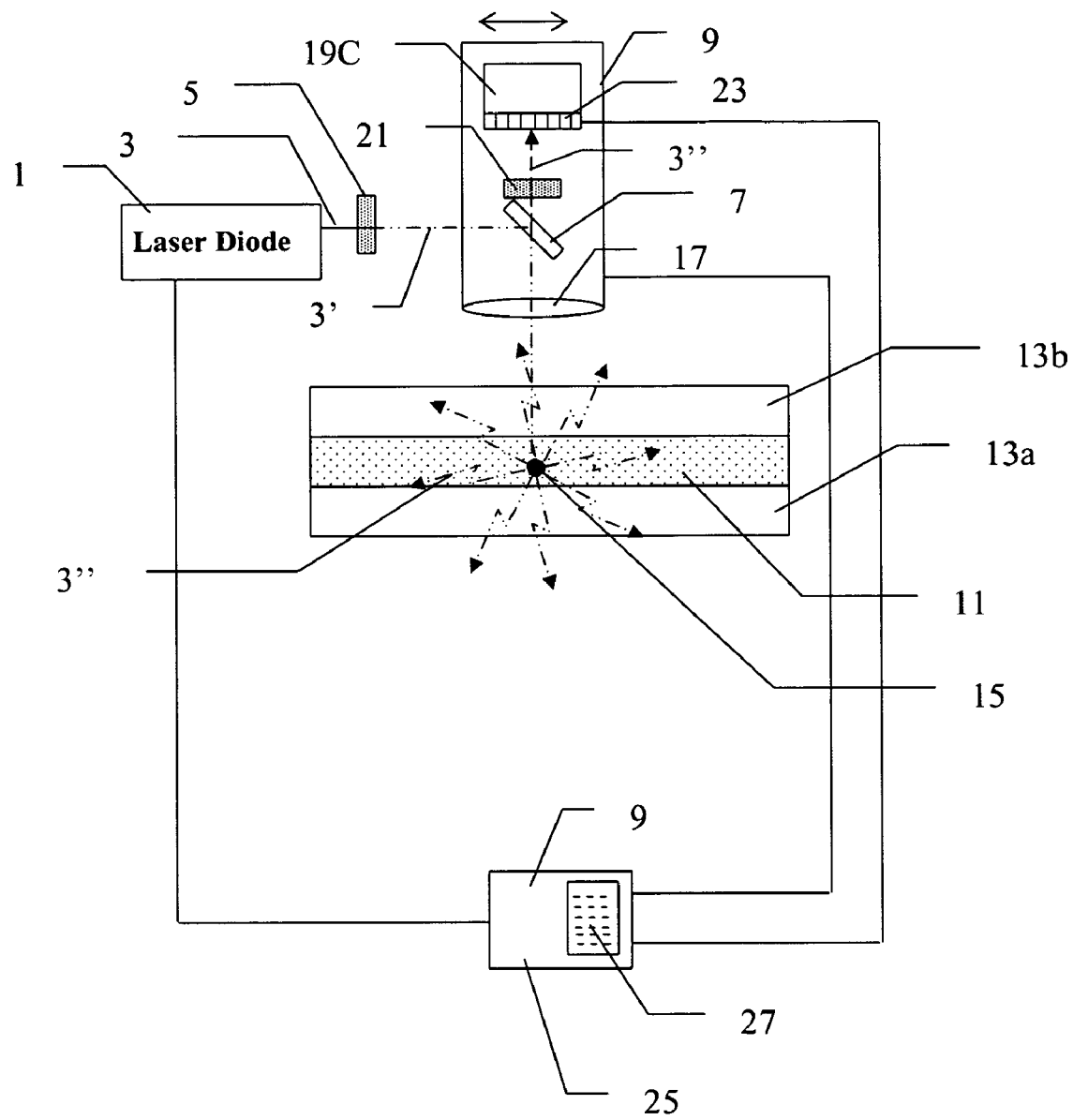

In a third embodiment of the present invention an apparatus for detecting fluorophore labelled substances is provided with two electromagnetic radiation detecting means 19A, 19B. In this apparatus a first line by line scan is performed using a first electromagnetic radiation detecting means 19A and a second scan is performed using a second electromagnetic radiation detecting means 19B. As shown in FIG. 2, both electromagnetic radiation detecting means can be contained in the same scanner head 9. Alternatively they may be mounted in separate scanner heads. The gain of the second electromagnetic radiation detecting means 19B is able to be adjusted by the control means on the basis of the intensity of the signal produced by said first electromagnetic radiation detecting means in order to prevent it being saturated when rescanning lines or pixels which produced a saturation signal in the first electromagnetic radiation detecting means. It is conceivable that when a scan takes place in a first direction, e.g. to the left in FIG. 2, then first electromagnetic radiation detecting means 19A performs the first scan of a line and second electromagnetic radiation detecting means 19B performs the rescanning at a lower gain, and when a scan takes place in the opposite direction, second electromagnetic radiation detecting means 19B performs the first scan of a line and-first electromagnetic radiation detecting means 19A performs the rescanning at a lower gain.

In a fourth embodiment of an apparatus in accordance with the present invention said first line by line scan is performed in a first electromagnetic radiation detecting means and said second scan is performed in a second electromagnetic radiation detecting means, wherein the gain of said second electromagnetic radiation detecting means is different to the gain of said first electromagnetic radiation detecting means. Thus the first scan could take place at a high gain and the second scan at a lower predetermined gain, the lower gain being kept constant. This would provide a device with an increased dynamic range when compared to the prior art and would remove the need for a control means to calculate a new gain to be used for the rescanning.

In a fifth embodiment of a device in accordance with the present invention a scanner head 9 comprises a CCD (charge coupled device) detector 19C and control means 25. The CCD detector comprises a plurality of charge coupled elements each of which, when exposed to an exciting source of electromagnetic radiation, produces a charge dependent on the intensity of the radiation which it is exposed to. The charge of each element may be outputted serially (i.e. element by element, line by line) and may be displayed as a pixel in an image. Said control means 25 is arranged to control the apparatus such that a first line by line scan of a target is performed with a CCD first exposure time in order to determine which lines or pixels in the scan comprise a detected emitter 15 of electromagnetic radiation that emits electromagnetic radiation exceeding a certain intensity and then a second scan is performed using a lower exposure time on only said lines or pixels which comprise a detected emitter 15 of electromagnetic radiation that emitted electromagnetic radiation exceeding a certain intensity during said first scan. This lower exposure time can be set by said control device to be short enough to prevent saturation of the CCD detector 19C. This embodiment may be modified to comprise two CCD detectors arranged in a similar fashion to the apparatus described in the third embodiment of the present invention.

In a further embodiment of the present invention, a first exposure of the complete target may be made at a high gain with a CCD detector and the charges on the CCD elements downloaded to an image processor and read serially. If any lines or pixels in the scan comprise a detected emitter of electromagnetic radiation that emits electromagnetic radiation exceeding a predetermined intensity, then the position of any such lines or pixels is recorded and a second complete scan is performed. Following this second scan, the charges on the CCD elements are downloaded serially but only the charges of the lines or pixels that comprised a detected emitter of electromagnetic radiation that emitted electromagnetic radiation exceeding the predetermined intensity in the first scan are read. The charges from the other lines or pixels are dumped, thereby saving the time that would otherwise be used to read them. In order to save further time, no all the lines or pixels are downloaded serially—the download may be stopped immediately after downloading the charge relating to the last line or pixel comprising a detected emitter of electromagnetic radiation that emits electromagnetic radiation exceeding the predetermined intensity. The charges of the following lines or pixels are dumped.

In another further embodiment of the present invention, instead of reducing the gain of the detector during a second scan which follows a first scan in which an emitter of electromagnetic radiation that emits electromagnetic radiation exceeding a certain, predetermined intensity is detected, the intensity of the exciting illumination is decreased. This may be achieved by reducing the power supplied to the source of exciting illumination (in which case it is preferable to have means for measuring the intensity of the exciting illumination in order to allow comparisons to be made between images or signals recorded at different levels of illumination intensity), or by putting a neutral filter of known intensity in the path between the exciting illuminating and the excited emitters of electromagnetic radiation.

In another further embodiment of the present invention both the detector gain and the intensity of the exciting illumination are able to be independently adjusted.

The invention is, of course, not restricted to the embodiments specifically described above and shown in the drawing, but many variations and modifications may be made within the scope of the general inventive concept as defined in the following claims.

What is claimed is:

1. A method for scanning an area (11) for emitters of electromagnetic radiation (15) by means of a scanner head (9) including an electromagnetic radiation detecting means (19) and control means (25), wherein said control means (25) is arranged:
   to control the movement of said scanner head (9):
   to control the gain of said electromagnetic radiation detecting means (19);
   to record in a memory (27) if the radiation (3") emitted by a detected emitter (15) of electromagnetic radiation and detected by electromagnetic radiation detecting means (19) exceeds a certain intensity; and,
   to record in a memory (27) the position of lines scanned by said scanner head (9) which contain a detected emitter of electromagnetic radiation (15) which emits radiation of an intensity which exceeds said certain intensity, wherein said method comprises the steps of:
   setting the gain of said electromagnetic radiation detecting means (19) to a high value;
   scanning first line by line the whole of said area for emitters of electromagnetic radiation;
   recording the position and intensity of electromagnetic radiation emitted from detected emitters of electromagnetic radiation (15);
   setting the gain of said electromagnetic radiation detecting means (19) to a lower value;
   rescanning only lines or pixels in said area (11) in which a detected emitter of electromagnetic radiation (15) emitted electromagnetic radiation (3") of an intensity greater than said certain intensity; and
   recording the position and intensity of electromagnetic radiation emitted from detected emitters of electromagnetic radiation (15).

2. The method of claim 1, further comprising setting said certain intensity to the saturation level of said electromagnetic radiation detecting means (19).

3. The method of claim 1, further comprising setting said certain intensity of said emitter to a value which is less than the saturation level of said electromagnetic radiation detecting means (19).

4. The method of claim 1, further comprising setting said certain intensity to between 99% and 75% of the saturation level of said electromagnetic radiation detecting means (19).

5. An apparatus for performing the method of claim 1, comprising a scanner head (9) comprising at least one electromagnetic radiation detecting means (19–19B) and control means (25), wherein said control means (25) is arranged:
- to control the movement of said scanner head (9):
- to control the gain of said electromagnetic radiation detecting means (19–19B);
- to record in a memory (27) when the radiation (3") emitted by a detected emitter (15) of electromagnetic radiation and detected by electromagnetic radiation detecting means (19–19B) exceeds a certain intensity; and,
- to record in a memory (27) the position of lines scanned by said scanner head (9) which contain a detected emitter of electromagnetic radiation which emits radiation of an intensity which exceeds said certain intensity,
- wherein said control means (25) performs a first line by line scan of the whole of said area at a high gain, determines which lines or pixels in the scan comprise a detected emitter (15) of electromagnetic radiation that emits electromagnetic radiation exceeding a certain intensity and performs a second scan at a lower gain on only said lines or pixels which comprise a detected emitter (15) of electromagnetic radiation that emitted electromagnetic radiation exceeding a certain intensity during said first scan.

6. The apparatus of claim 5, wherein said first line by line scan is performed in a first electromagnetic radiation detecting means (19A) and said second scan is performed in a second electromagnetic radiation detecting means (19B), wherein the gain of said second electromagnetic radiation detecting means (19B) is adjusted on the basis of the intensity of the signal produced by said first electromagnetic radiation detecting means.

7. The apparatus of claim 5, wherein said first line by line scan is performed in a first electromagnetic radiation detecting means (19A) and said second scan is performed in a second electromagnetic radiation detecting means (19B), wherein the gain of said second electromagnetic radiation detecting means (19B) is different to the gain of said first electromagnetic radiation detecting means (19A).

8. The apparatus of claim 5, comprising the scanner head (9) comprising an CCD detector (19C) and control means (25), wherein said control means (25) is arranged:
- to control the movement of said scanner head (9):
- to control the exposure time of said CCD detector (19C);
- to record in a memory (27) when the radiation (3") emitted by a detected emitter (15) of electromagnetic radiation and detected by said CCD detector (19C) exceeds a certain intensity; and,
- to record in a memory (27) the position of lines scanned by said scanner head (9) which contain a detected emitter of electromagnetic radiation which emits radiation of an intensity which exceeds said certain intensity,
- wherein said control means (25) performs a first line by line scan of the whole of said area with a first exposure time, determines which lines or pixels in the scan comprise a detected emitter (15) of electromagnetic radiation that emits electromagnetic radiation exceeding a certain intensity and performs a second scan at a lower exposure time on only said lines or pixels which comprise a detected emitter (15) of electromagnetic radiation that emitted electromagnetic radiation exceeding a certain intensity during said first scan.

* * * * *